United States Patent
Frick et al.

(10) Patent No.: US 11,400,283 B2
(45) Date of Patent: Aug. 2, 2022

(54) PULSE GENERATING DEVICE FOR DELIVERY OF ELECTRICAL PULSES TO A DESIRED TISSUE OF A MAMMAL

(71) Applicant: SCANDINAVIAN CHEMOTECH AB, Lund (SE)

(72) Inventors: Mohan Frick, Gothenburg (SE); Bertil R R Persson, Lund (SE)

(73) Assignee: Scandinavian Chemotech AB, Lund (SE)

(*) Notice: Subject to any disclaimer, the term of this patent is extended or adjusted under 35 U.S.C. 154(b) by 408 days.

(21) Appl. No.: 16/633,365

(22) PCT Filed: Jul. 27, 2018

(86) PCT No.: PCT/EP2018/070446
§ 371 (c)(1),
(2) Date: Jan. 23, 2020

(87) PCT Pub. No.: WO2019/020802
PCT Pub. Date: Jan. 31, 2019

(65) Prior Publication Data
US 2021/0154471 A1    May 27, 2021

(30) Foreign Application Priority Data
Jul. 28, 2017   (SE) .................................... 1750966-2

(51) Int. Cl.
*A61N 1/32* (2006.01)
*A61N 1/05* (2006.01)

(52) U.S. Cl.
CPC ........... *A61N 1/327* (2013.01); *A61N 1/0502* (2013.01)

(58) Field of Classification Search
CPC ...... A61N 1/00; A61N 1/0404; A61N 1/0412; A61N 1/0476; A61N 1/05002;
(Continued)

(56) References Cited

U.S. PATENT DOCUMENTS 6,117,660 A    9/2000   Walters et al.
10,245,098 B2  4/2019   Davalos et al.
(Continued)

FOREIGN PATENT DOCUMENTS

EP    3187138 A1    7/2017
GB    2496449 A     5/2013
(Continued)

OTHER PUBLICATIONS

Chunlan J., "A review of basic to clinical studies of irreversible electroporation therapy", IEEE transactions on biomedical engineering (2015), No. 1, vol. 62, pp. 4-20.
(Continued)

*Primary Examiner* — Brian T Gedeon
(74) *Attorney, Agent, or Firm* — Merchant & Gould P.C.

(57) ABSTRACT

A pulse generating device for delivery of electrical pulses to a desired tissue and configured to be connected to needle electrodes arranged at the desired tissue. The device comprises a determining module configured to determine a primary voltage amplitude of a first pulse and a number of consecutive pulses to be generated. Further, the device comprises a pulse generator configured to generate one or more of the determined number of consecutive pulses such that the generated first pulse has the primary voltage amplitude and that the generated consecutive pulses have a respective voltage amplitude consecutively decreasing between consecutive pulses, whereby an increase in a current value of the generated consecutive pulses above a threshold value is avoided. Furthermore, the device comprises a terminating module configured to terminate generation of the one or more pulses when a value of a total absorbed energy exceeds a threshold value.

12 Claims, 4 Drawing Sheets

(58) Field of Classification Search
CPC ........... A61N 1/327; A61N 1/36002; A61N 1/36017; A61N 1/3712; A61B 18/1206; A61B 18/1477; A61B 2018/00613; A61B 2018/00642; A61B 2018/143; A61B 2018/00636; A61B 2018/00875; A61B 2018/1425
See application file for complete search history.

(56) References Cited

U.S. PATENT DOCUMENTS

| | | |
|---|---|---|
| 2002/0165531 A1 | 11/2002 | Goble |
| 2007/0242743 A1 | 10/2007 | Scherman |
| 2009/0044717 A1 | 2/2009 | Husseini et al. |
| 2009/0248012 A1 | 10/2009 | Maor et al. |
| 2009/0281477 A1 | 11/2009 | Mikus et al. |
| 2010/0196984 A1 | 8/2010 | Rubinsky et al. |
| 2010/0267106 A1 | 10/2010 | Mueller-Hartmann |
| 2012/0095459 A1 | 4/2012 | Callas et al. |
| 2012/0179154 A1 | 7/2012 | Goldberg et al. |

FOREIGN PATENT DOCUMENTS

| | | |
|---|---|---|
| WO | 98/14238 A1 | 4/1998 |
| WO | 99/52589 A1 | 10/1999 |
| WO | 2008/090444 A1 | 7/2008 |
| WO | 2011/056464 A2 | 5/2011 |
| WO | 2015/175570 A1 | 11/2015 |

OTHER PUBLICATIONS

First Notice (Office Action) from corresponding Swedish Patent Application No. 1750966-2, dated Mar. 16, 2018.
International-Type Search Report from corresponding Swedish Patent Application No. 1750966-2, dated Mar. 16, 2018.
International Search Report and Written Opinion from corresponding International Application No. PCT/EP2018/070446, dated Nov. 7, 2018.
International Preliminary Report on Patentability from corresponding International Application No. PCT/EP2018/070446, dated Nov. 7, 2018.
Second Notice (Office Action) from corresponding Swedish Patent Application No. 1750966-2, dated Jan. 31, 2019.
Swedish Search Report from corresponding Swedish Patent Application No. 1750966-2, dated Mar. 16, 2018.

PULSE GENERATING DEVICE FOR DELIVERY OF ELECTRICAL PULSES TO A DESIRED TISSUE OF A MAMMAL

This application is a National Stage Application of International Application No. PCT/EP2018/070446, filed Jul. 27, 2018, which claims benefit of U.S. Pat. No. 1,750,966-2, filed Jul. 28, 2017 in Sweden and which applications are incorporated herein by reference. To the extent appropriate, a claim of priority is made to each of the above disclosed applications.

TECHNICAL FIELD

Embodiments herein relate to a pulse generating device and to methods therein. Especially, embodiments herein relate to the delivery of electrical pulses to a desired tissue of a mammal.

BACKGROUND

Pulsed electric fields applied to biological cells and tissues create transverse channels or pores in the cell membrane, a phenomenon called electro-permeabilization or electroporation. The explanation to pore formation is the reorganization of interfacial water in structures of the lipid bilayer membranes due to the pulsed applied electric fields.

Electroporation increases the probability for the migration of hydrophilic molecules through the cell membranes. Thus, molecules outside the cells move into the cytoplasm, and out of the cytoplasm migrate intracellular antigenic molecules to the extracellular space. The rate of resealing the membranes and recovery of the cells depend on the strength of the applied voltage, and the number and length of the applied electric pulses.

Most electroporation protocols for experimental, clinical, and biotechnological applications use pulses, e.g. direct current (DC) pulses, of about 1000 V/cm, with durations of at least 100 μs. But membrane permeabilization also occurs with shorter pulses with pulse-lengths, in the range of 100 ns, however, at a much higher electric field-strength.

The concept of electro-permeabilization is employed in tumour treatment by increasing the permeability of tumour cells, and thus to enhance the access of administered cytotoxic agents to solid tumours. Generally, a low dose of bleomycin, a highly toxic antibiotic agent that normally does not penetrate the tumour cell membrane, is administered either intravenously (15000-25000 International Units (IU)), or directly to the tumours (260-1000 IU/cm$^3$) before electric pulses are applied to them. However, a combination of intravenous and direct administration of the agent may be applied. By applying the electric pulses, the therapeutic effect of the chemotherapy can be enhanced.

This procedure applied clinically is usually called Electro-Chemo-Therapy (ECT), and commonly pulse train packages of 8 rectangular pulses are delivered within 2 s with a nominal electric field strength of about 1000 V/cm (that means a voltage of 1000 V applied between pin electrodes with distance of about 4-12 mm, e.g. 8-10 mm), and with a duration of 100 μs for each pulse. In an example protocol, totally 96 electric pulses are delivered over a number (e.g. 12) of pairs of electrodes in the applicator. The general hypothesis is that the efficacy of ECT is due to the applied voltage and the distance between the electrodes. The absorbed energy per pulse is estimated to about 500 J/kg and the current about 16 A. This seems, however, to be too detrimental to tissues, particularly in head and neck treatments. The use of a too high electric field strength and a too high current cause inflammatory response and immune suppression that limit the infiltration of killer T-cells to the treated tumour.

WO9814238A1 discloses an apparatus comprising means for ionizing radiation and a high voltage generator for generating brief voltage pulses for voltage application of electrodes included in the apparatus. The electrodes are designed to be secured at or introduced into tissue in a restricted region of a human or an animal and to form between them an electric field in the tissue. The means are provided to emit ionizing radiation to a tumour in the tissue in that region which is to be treated, while the electrodes are disposed to be placed in or at the tumour so that the electric field passes through the tumour.

WO9952589A1 discloses an apparatus comprising a voltage generator for generating brief voltage pulses for the impression of voltage on electrodes included in the apparatus, and a measurement unit, which is coupled to the electrodes. These are designed to be secured at or inserted in tissue in a restricted region of a human or an animal in order therebetween to form electric fields in the tissue. The measurement unit is disposed to determine the impedance between the electrodes, which is substantially determined by the electric properties of the tissue, which is located between the electrodes. A registration and calculator device forms a control unit, which, based on the impedance determined by the measurement unit, controls the output voltage of the voltage generator such that the electric field, which is formed in the tissue, always has a predetermined value. The treatment with the electric field realizes a perforation of cell membranes in the tissue which thereby permits the passage of substances fed to the body, e.g. cytostatic or genetic material.

A drawback with previously known devices is that a too high electric field strength and a too high current may be applied to the treatment volume of the mammal causing inflammatory response and immune suppression that limit the infiltration of killer T-cells to the treated tumour.

SUMMARY

An aim of some embodiments disclosed herein is to overcome or mitigate at least some of the drawbacks with the prior art.

Thus, the aim of some embodiments disclosed herein is to provide a pulse generating device having an improved control of the generation of electrical pulses. Thereby, by means of embodiments disclosed a current density and a specific absorbed energy in the tissue is controlled to optimally enhance a therapeutic effect and to minimize the probability of detrimental side effects associated with the prior art.

According to an aspect of embodiments herein, the object is achieved by a pulse generating device for delivery of electrical pulses to a desired tissue of a mammal, wherein the pulse generating device is configured to be connected to at least two needle electrodes configured to be arranged at the desired tissue of the mammal.

The pulse generating device comprises a determining module configured to determine a primary voltage amplitude of a first electrical pulse to be generated between the at least two needle electrodes, and to determine a number of consecutive electrical pulses to be generated. The primary voltage amplitude and the number of consecutive electrical pulses to be generated may be determined such that a predetermined current density in the desired tissue will not be exceeded and such that a predetermined specific power density may not be exceeded when the number of consecutive electrical pulses are applied to the desired tissue.

Further, the pulse generating device comprises a pulse generator in electrical communication with the at least two needle electrodes and configured to generate one or more of the determined number of consecutive electrical pulses such that the generated first electrical pulse has the primary voltage amplitude and that the one or more generated consecutive electrical pulses have a respective voltage amplitude consecutively decreasing between consecutively generated electrical pulses. Thereby, an increase in a current value of the one or more of the determined number of electrical pulses above a threshold value is avoided. This may also be expressed as a current density of the one or more generated consecutive electrical pulses above a threshold value is avoided.

Furthermore, the pulse generating device comprise a terminating module configured to terminate generation of the one or more of the determined number of electrical pulses when a value of a total absorbed energy, caused in the desired tissue by the one or more generated electrical pulses, exceeds a desired threshold value.

For example, the terminating module may terminate the generation of the one or more of the determined number of electrical pulses when a cumulated value of a total specific absorbed energy, caused in the desired tissue by the one or more generated electrical pulses, exceeds a desired threshold value, e.g. 1000 J/kg. Alternatively or additionally, the terminating module may terminate the generation of the one or more of the determined number of electrical pulses when a recorded current exceeds a predetermined threshold level, e.g. 6 A.

According to another aspect of embodiments herein, the object is achieved by a method performed by a pulse generating device for delivery of electrical pulses to a desired tissue of a mammal, wherein the pulse generating device is configured to be connected to at least two needle electrodes configured to be arranged at the desired tissue of the mammal.

The pulse generating device determines a primary voltage amplitude of a first electrical pulse to be generated between the at least two needle electrodes, and determines a number of consecutive electrical pulses to be generated.

Further, the pulse generating device generates one or more of the determined number of consecutive electrical pulses such that the generated first electrical pulse has the primary voltage amplitude and that the one or more generated consecutive electrical pulses have a respective voltage amplitude consecutively decreasing between consecutively generated electrical pulses. Thereby, an increase in a current value of the one or more generated consecutive electrical pulses exceeds the threshold value is avoided.

Furthermore, the pulse generating device terminates generation of the one or more of the determined number of electrical pulses when a value of current a total absorbed energy, caused in the desired tissue by the one or more generated electrical pulses, exceeds a desired threshold value.

According to another aspect of embodiments herein, the object is achieved by a computer program, comprising instructions which, when executed on at least one processor, causes the at least one processor to carry out the method performed by the pulse generating device.

According to another aspect of embodiments herein, the object is achieved by a carrier comprising the computer program, wherein the carrier is one of an electronic signal, an optical signal, a radiofrequency signal or a computer readable storage medium.

Since the pulse generator is configured to generate the one or more of the determined number of consecutive electrical pulses, such that the generated first electrical pulse has the primary voltage amplitude and that the one or more generated consecutive electrical pulses have a respective voltage amplitude, consecutively decreasing between consecutively generated electrical pulses, an increase in a current value of the one or more generated consecutive electrical pulses above a threshold value is avoided. Further, since the terminating module is configured to terminate the generation of the one or more of the determined number of electrical pulses when a value of a total absorbed energy exceeds a desired threshold value, an optimal therapeutic effect is achieved while avoiding detrimental inflammatory effects due to a too high total absorbed energy which otherwise would enhance the immune suppression.

An advantage with some embodiments disclosed herein is an optimized enhanced therapeutic effect while avoiding detrimental side effects.

A further advantage with some embodiments disclosed herein is that the use of specific absorbed energy (J/kg) as a dosimetry quantity harmonizes with other physically based therapeutics such as absorbed dose (Gy=J/kg) in radiation therapy.

BRIEF DESCRIPTION OF DRAWINGS

Examples of embodiments herein will be described in more detail with reference to attached drawings in which.

DETAILED DESCRIPTION

An object addressed by embodiments herein is how to improve performance in a pulse generating device for delivery of electrical pulses to a desired tissue of a mammal.

In this disclosure, a new concept called Dynamic Electro Enhanced Chemotherapy (D-EECT™) will be described. In a D-EECT protocol, a pulse-train of electrical pulses of gradually decreasing voltage, e.g. pseudo exponentially decreasing voltage, is applied and the electrical current in each pulse is controlled to not exceed an upper current threshold value, e.g. a pre-set current threshold value in the order of 6-14 A, e.g. 6-10 A. The reason for controlling the electrical current of each pulse is that the magnitude of the electrical current generated in each pulse influence the clinical outcome of the treatment and should therefore be controlled.

The electrical current in the pulse depends on the conductivity of the organ or tissue to be treated. Further, the conductivity varies widely between various tissues and organs.

For example, conductivity values of in vivo human tissues vary between 0.02-1.5 S/m at a low frequency<1 kHz. In tissue phantoms (saline, film), examined by Magnetic Resonance Imaging (MRI) combined with electrical impedance tomography, the conductivity is about 0.09 S/m. Further, in prostate tissue the electrical conductivity increases from 0.3 to 0.9 S/m due to exposure of high voltage pulses, e.g. pulses of 1100 V/cm.

It is thus of importance to know the tissue conductance before and during treatment in order to select parameters in the D-EECT protocol so that the current is limited to about 6-14 A, e.g. 6-10 A. A memory, e.g. a database, may provide pre-treatment values to the protocol. During the treatment the current as well as the voltage is recorded in each pulse and the conductance during treatment may be evaluated by evaluating a current to voltage ratio. For example, when the current to voltage ratio increases 1% the conductance increases 1%, and when the current to voltage ratio decreases 1% the conductance is decreases 1%.

Figure 1:
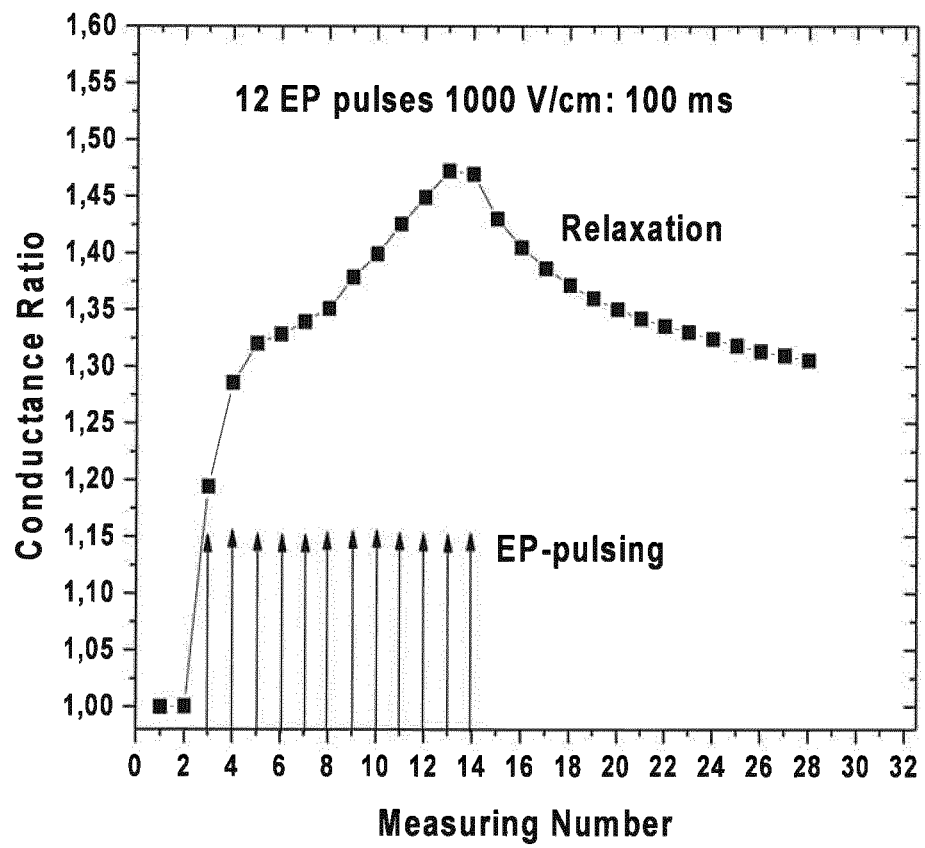
FIG. 1 schematically illustrates the conductance ratio relative to the pre-treatment value to visualize the degree of the effect achieved by the treatment and the degree of the reversible effect.

FIG. 1 schematically shows the ratio of the conductance recorded after each pulse relative to the pre-treatment value to visualize the degree of the effect achieved by the treatment and the degree of the reversible effect after the treatment, i.e. the relaxation after the measuring number 14. The conductance is given by 1/resistance=current/voltage.

In the following, embodiments herein are illustrated by exemplary embodiments. It should be noted that these embodiments are not mutually exclusive. Components from one embodiment may be tacitly assumed present in another embodiment and it will be obvious to a person skilled in the art how those components may be used in the other exemplary embodiments.

It should furthermore be noted that, to anyone skilled in the art, there are several realizations of the embodiments below with principally equivalent functionality.

Figure 2:
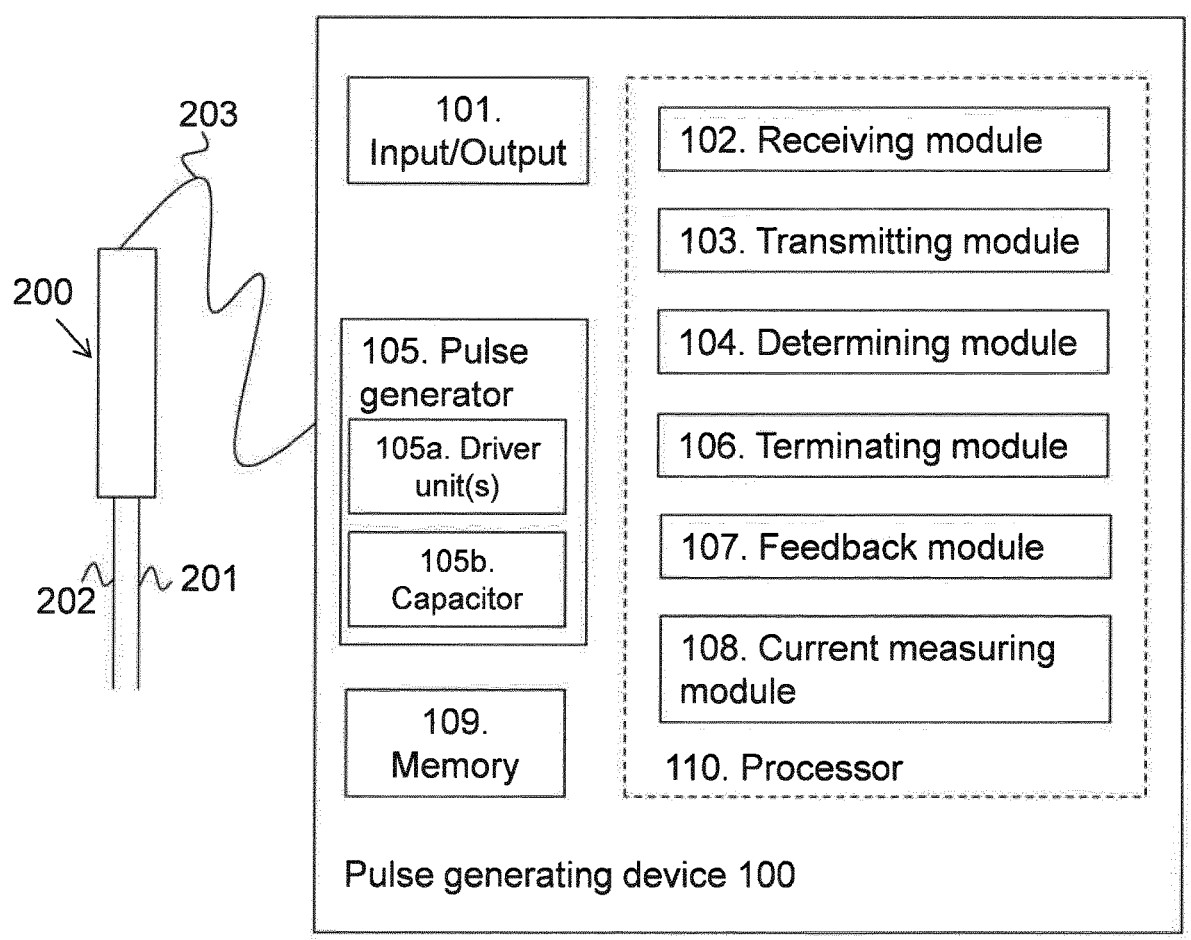
FIG. 2 schematically illustrates embodiments of the pulse generating device connected to an electrode device.

FIG. 2 schematically illustrates embodiments of a pulse generating device 100 for delivery of electrical pulses to a desired tissue of a mammal.

The pulse generating device 100 is configured to be connected to an electrode device 200. The electrode device 200 comprises at least two needle electrodes 201,202 configured to be arranged at the desired tissue of the mammal. For example, the at least two needle electrodes 201,202 may be configured to be inserted in the desired tissue of the mammal. In FIG. 2 only two needle electrodes 201, 202 are shown but it should be understood that the number of needle electrodes may be more than two, e.g. four. Further, the pulse generating device 100 may be connected to the electrode device 200 via electrical wiring or cable 203.

The pulse generating device 100 may comprise an input/output interface 101, to facilitate communications with a user such as an operator of the pulse generating device 100. The interface may, for example, comprise an output device such as a monitor e.g. a display device, an input device such as a keyboard, keypad, a mouse, or a combined input and output device such as a touch screen. The input and output interface 101 may additionally or alternatively comprise means for wired or wireless communication with another device (not shown).

The pulse generating device 100 may be configured to receive, by means of a receiving module 102 configured to receive, information or data from one or more other devices. The receiving module 102 may be implemented by or arranged in communication with a processor 110 of the pulse generating device 100. The processor 110 will be described in more detail below.

The pulse generating device 100 may be configured to transmit, by means of a transmitting module 103 configured to transmit, information or data to one or more other devices. The transmitting module 103 may be implemented by or arranged in communication with the processor 110 of the pulse generating device 100.

The pulse generating device 100 is configured to, e.g. by means of a determining module 104 configured to, determine a primary voltage amplitude of a first electrical pulse to be generated between the at least two needle electrodes 201,202, and to determine a number of consecutive electrical pulses to be generated. The determining module 104 may be implemented by or arranged in communication with the processor 110 of the pulse generating device 100.

In some embodiments, the primary voltage amplitude of the first electrical pulse gives a primary current of the first electrical pulse that is within a desired current interval. For example, in some embodiments, the primary current should be above approximately 4 A and below an upper threshold value of 6-10 A, e.g. below 6 A.

The pulse generating device 100 may further be configured to, e.g. by means of the determining module 104, to determine a pulse shape of the electrical pulses to be generated, and/or a pause period e.g. a time period during which the generation of pulses is to be paused and thus during which time period no pulses is to be generated.

In some embodiments, the pulse generating device 100, e.g. by means of the determining module 104, is configured to determine the primary voltage amplitude of the first electrical pulse to be generated between the at least two needle electrodes and the number of consecutive electrical pulses to be generated based on a characteristic frequency $f_c=\sigma/C$ of the desired tissue at 1 kHz, wherein $\sigma$ is the conductivity of the desired tissue, C is the capacitance of a capacitor of the pulse generating device 100.

The pulse generating device 100, e.g. by means of the determining module 104, may be configured to determine one of the electrodes 201,202 comprised in an electrode pair to be generating a positive potential output and another one of the electrodes 201,202 comprised in an electrode pair to be generating a zero potential output.

In some embodiments, the pulse generating device 100, e.g. by means of the determining module 104, is configured to retrieve a conductivity value specific for the desired tissue from a database, such as a memory, e.g. a memory 109 that will be described in more detailed below. Further, the determining module 104 is configured to determine one or more treatment parameters based on the retrieved conductivity value. For example, the determining module 104 may be configured to determine the one or more treatment parameters based on the retrieved conductivity value such that a current of generated pulses is above a lower current threshold value and below an upper current threshold value. For example, the lower current threshold value may be 4 A, and the upper current threshold value may be in the range of 6-10 A, e.g. 6 A.

The pulse generating device 100 is configured to, e.g. by means of a pulse generator 105 configured to, generate one or more electrical pulses. The pulse generator 105 may be arranged in communication with the processor 110 of the pulse generating device 100.

The pulse generating device 100, e.g. by means of the pulse generator 105, is arranged in electrical communication with the at least two needle electrodes 201,202 and configured to generate one or more of the determined, e.g. predetermined, number of consecutive electrical pulses such that the generated first electrical pulse has the primary voltage amplitude and that the one or more generated consecutive electrical pulses have a respective voltage amplitude consecutively decreasing between consecutively generated electrical pulses. Thereby, an increase in a current value of the one or more generated consecutive electrical pulses above a threshold value is avoided.

In some embodiments, the pulse generating device 100, e.g. by means of the pulse generator 105, is configured to generate the one or more of the determined number of consecutive electrical pulses with a respective voltage amplitude that is decreasing with a pre-set amplitude value between two consecutive electrical pulses, wherein the pre-set amplitude value is in the range of 100-1200V, e.g. in the range of 400-1200 V.

The pulse generating device 100, e.g. by means of the pulse generator 105, may be configured to generate the one or more of the determined number of consecutive electrical pulses with a respective voltage amplitude that is exponentially decreasing between two consecutive electrical pulses. For example, the respective voltage amplitude may be exponentially decreasing between two generated consecutive electrical pulses as a function of $e^{-f_c t}$, wherein $f_c = \sigma/C$, $\sigma$ is the conductivity of the desired tissue, C is the capacitance of a capacitor of the pulse generator 105, and t is the time between the two generated consecutive electrical pulses. Sometime in this disclosure $f_c$ is referred to as a constant. Since the constant $f_c$ given above as $f_c = \sigma/C$ is dependent on the tissue conductivity $\sigma$, that may vary depending on the tissue, the generated pulses and on the number of pulses, the pulse generator 105 may alternatively be configured to generate the one or more of the determined number of consecutive electrical pulses according to a pre-programmed pulse sequence wherein the respective voltage amplitude of consecutive electrical pulses is a pseudo exponentially decreasing voltage with a time constant derived from conductivity values taken from a data base, such as a memory. For example, the constant may be derived from the conductivity values and the capacitance load of the device.

It should be understood that the constant $f_c$ may be varied for different types of tumours to get the most optimal treatment. Thus, values of constants for various tumours may be derived from conductivity values taken from the data base, e.g. the memory 109.

In some embodiments, the pulse generating device 100, e.g. by means of the pulse generator 105, is configured to generate electrical pulses with varying polarity and varying amplitude from e.g. 100 V to 1200 V.

The pulse generator 105 may be configured to generate positive voltage pulses between each separate electrode pair with a code given by the processor 110. The code may relate to one or more parameters of one or more pulses to be generated. The parameters may relate to a polarity, a voltage, an electrode number, etc. of the one or more pulses to be generated.

In some embodiments, the pulse generating device 100, e.g. by means of the pulse generator 105, is configured to first excite a first one of the two electrodes 201,202 with a positive voltage and a second one of the two electrodes 201,202 with zero voltage. The pulse generator 105 may then in a second excitation excite the second one of the two electrodes 201,202 with the positive voltage and the first one of the two electrodes with zero voltage. Thereby, an improved homogeneity of the therapeutic effect in the target volume is achieved. It should be understood that in a third excitation the pulse generator 105 may excite the first one of the two electrodes 201,202 with a positive voltage and the second one of the two electrodes 201,202 with zero voltage, and this may be repeated for every following excitation. Further, it should be understood that each excitation corresponds to one generated pulse.

In some embodiments, the pulse generating device 100, e.g. by means of the pulse generator 105, is configured generate pulses to four needle electrodes positioned in a respective corner of a square of the desired tissue. By such positioning of the electrodes, the treatment volume may be easily changed. In order to promote homogeneous E-field distribution in the treatment volume with four electrodes, all 12 possible combinations of positive and negative pulse applications, including horizontal, vertical and diagonal will be applied such as in the first excitation of each electrode pair the voltage of one of the electrodes, is positive and corresponding electrode is at negative or zero voltage, in a second excitation the voltage at the electrodes are reversed. This pattern may be executed by the pulse generating device 100 for all electrode combinations to promote homogeneity of the electro-enhanced chemo-therapeutic effect in the target volume.

One or more driver units 105a may be comprised in or connected to the pulse generator 105. Each of the one or more driver units 105a may be configured to generate an electrical pulse between a pair of electrodes 201,202. Thus, in case of several pairs of electrodes 201,202, the pulse generator 105 may comprise a driver unit 105a for each pair of electrodes, and consequently the number of driver units 105a corresponds to the number of pairs of electrodes. However, it should be understood that the number of driver units 105a may be less than or more than the number of electrode pairs.

One or more capacitors 105b may be comprised in or connected to the pulse generator 105. Each one of the one or more capacitors 105b may be charged to a desired voltage value, e.g. the pre-set voltage value, and configured to be discharged to create one or more electrical pulses. For example, the capacitor 105b may be configured to be discharged stepwise to create a pulse train.

The pulse generating device 100 is configured to, e.g. by means of a terminating module 106 configured to, terminate generation of one or more electrical pulses. The terminating module 106 may be implemented by or arranged in communication with the processor 110 of the pulse generating device 100.

The pulse generating device 100, e.g. by means of the terminating module 106, may be configured to terminate generation of the one or more of the determined number of electrical pulses when a value of a total absorbed energy, caused in the desired tissue by the one or more generated electrical pulses, exceeds a desired threshold value.

In some embodiments, the absorbed energy is a specific absorbed energy, e.g. an absorbed energy value given per kilogram.

The pulse generating device 100, e.g. by means of the terminating module 106, may further be configured to terminate generation of the one or more of the determined number of electrical pulses when one of the respective current values of the generated electrical pulses is outside the desired current interval.

As will be described below, the pulse generating device 100 may comprise a feedback module 107 giving feedback relating to one or more generated electrical pulses to the terminating module 106. In such embodiments, the terminating module 106 is configured to determine the total absorbed energy based on the received information relating to the determined respective absorbed energy, and to determine whether the total absorbed energy exceeds the desired threshold value.

The pulse generating device 100 is configured to, e.g. by means of a feedback module 107 configured to, give feedback relating to one or more generated electrical pulses. The feedback module 107 may be implemented by or arranged in communication with the processor 110 of the pulse generating device 100.

In some embodiments, the pulse generating device 100, e.g. by means of the feedback module 107, is configured to determine a respective absorbed energy of each one of the one or more generated electrical pulses and to send information relating to the determined respective absorbed energy, and possibly the respective generated electrical pulse, to the terminating module 106.

The pulse generating device 100, e.g. by means of the feedback module 107, may be configured to determine the respective absorbed energy as a specific absorbed energy, SE, given by the equation for each pulse:

$$SE_p = \frac{J^2 \cdot t_p}{\sigma \cdot \rho} \text{ given J/kg,}$$

wherein p identifies the pulse, $\sigma$ is the conductivity of the desired tissue given in S/m, J is the current density given in A/m² between the needles, e.g. between the needle electrodes 201,202, that is proportional to the recorded current J(A·cm⁻²)≈1.2>I (A), $\rho$ is the tissue density given in 1060 kg/m³, and $t_p$ is the length of the applied pulse given in s.

In some embodiments, the pulse generating device 100, e.g. by means of the feedback module 107, is configured to receive or retrieve information relating to a respective current of each one of the one or more generated electrical pulses and to send information relating to the respective current, and possibly relating to the respective generated electrical pulse, to the terminating module 106. The device 100, e.g. by means of the feedback module 107, may be configured to receive or retrieve information relating to a current of a pulse from a current measuring module 108, which will be described below.

In some embodiments, the pulse generating device 100, e.g. by means of the feedback module 107, is configured to determine a respective voltage value of each one of the one or more generated electrical pulses. The feedback module 107 may be configured to determine the respective voltage value V as V=MF·$I_L$/$\sigma$ where $I_L$ is a current limit value, e.g. 6 A, $\sigma$ is the conductivity (S/m) of the target tissue and MF is a modification factor determined by the electrode configuration and clinical experience. For example, the parameters may have the following values $\sigma$=1 S/m, $I_L$ 0.6 A, MF≈100, or $\sigma$=0.01 S/m, $I_L$=6 A, MF≈2 just to give some examples.

The feedback module 107 may be configured to send information relating to the determined respective voltage, and possibly the respective generated electrical pulse, to the terminating module 106.

The pulse generating device 100, e.g. by means of the feedback module 107, may further be configured to store one or more of the determined respective current value, determined respective voltage value, and information relating to the respective generated electrical pulse, in a database, such as a memory, e.g. a memory 109 which will be described in more detail below.

The pulse generating device 100 is configured to, e.g. by means of a current measuring module 108 configured to, measure the current of a pulse, e.g. the current of a generated pulse. The current measuring module 108 may be implemented by or arranged in communication with the processor 110 of the pulse generating device 100.

The pulse generating device 100 may also comprise or be connected to means for storing data. In some embodiments, the pulse generating device 100 may further comprise or be connected to a memory 109 configured to store the data relating to the delivery of electrical pulses to the desired tissue of the mammal. The data may be processed or non-processed data and/or information relating thereto. The memory 109 may comprise one or more memory units. Further, the memory 109 may be a computer data storage or a semiconductor memory such as a computer memory, a read-only memory, a volatile memory or a non-volatile memory. The memory 109 is arranged to be used to store obtained information, data, configurations, and applications to perform the methods herein when being executed in the pulse generating device 100.

For example, the memory 109 may comprise information about the tumour regression and descriptor variables of the patient, tumour, and impedance parameters. The information and description variables may be modelled with multivariate statistical methods such as projection of latent variables regression in order to develop confident prediction of values for the response, and best outcome of the treatment. For example, statistical methods using multivariate data processing methods such as Principal Component Analysis (PCA) and modelled with the method of Projection to Latent Structures (PLS), also called Partial Least Square Regression (PLSR), may be used.

Embodiments of the memory 109 will be described in more detail below.

Embodiments herein for delivery of electrical pulses to the desired tissue of the mammal may be implemented through one or more processors, such as the processor 110 in the arrangement depicted in FIG. 1, together with computer program code for performing the functions and/or method actions of embodiments herein. The program code mentioned above may also be provided as a computer program product, for instance in the form of a data carrier carrying computer program code for performing the embodiments herein when being loaded into the pulse generating device 100. One such carrier may be in the form of an electronic signal, an optical signal, a radio signal or a computer readable storage medium. The computer readable storage medium may be a CD ROM disc, SIM card or a memory stick.

The computer program code may furthermore be provided as program code stored on a server and downloaded to the pulse generating device 100.

Those skilled in the art will also appreciate that the input/output interface 101, the receiving module 102, the transmitting module 103, the determining module 104, the pulse generator 105, the terminating module 106, the feedback module 107, and the current measuring module 108 above may refer to a combination of analogue and digital circuits, and/or one or more processors configured with software and/or firmware, e.g. stored in the memory 109, that when executed by the one or more processors such as the processors in the pulse generating device 100 perform as described above. One or more of these processors, as well as the other digital hardware, may be included in a single Application-Specific Integrated Circuitry (ASIC), or several processors and various digital hardware may be distributed among several separate components, whether individually packaged or assembled into a System-on-a-Chip (SoC).

Uptake of a Therapeutic Agent

Figure 3:
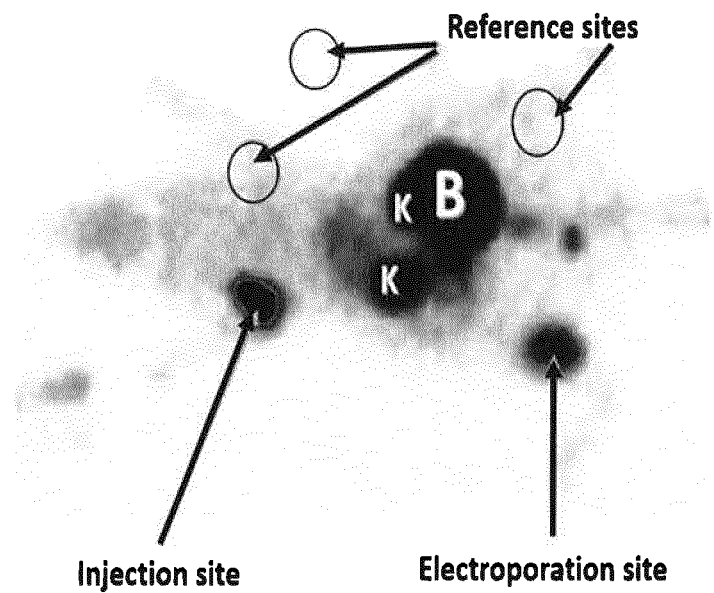
FIG. 3 schematically illustrates a gamma camera image of a rat taken after electro enhanced chemotherapy which demonstrates the enhanced uptake of the administered pharmaceutical in the treated target.

The importance of various variables for the outcome of Electro-Enhancement has been investigated by studying the uptake of a radioactive tracer, e.g. 99Tcm- diethylene-triamine-penta-acetic-acid (99Tcm-DTPA), in rat muscle. The applied voltage between pin electrodes, e.g. the electrodes 201,202, inserted in muscle tissue of living rats at a distance of 8 mm varied between 100 and 1200 V, the pulse length varied between 0.1-20 ms, and the number of applied pulses varied between 2-12 pulses. FIG. 3 schematically illustrates a Gamma Camera image of a rat taken 6 hours after an electroporation treatment with electrical field strength of 800 V/cm and 12 pulses of 250 µs length. Further, FIG. 3 shows a high activity in the electroporated site, while low activity is recorded in the reference sites. In FIG. 3, the injection site, the electroporation site and three reference sites are shown. Further, the kidneys are indicated by K and the bladder by B.

Surprisingly the inventors have found that a correlation coefficient for the relative uptake of an administrated drug versus the applied electrical field strength become negative when the applied filed strength is increased, which confirms that a too high field strength is detrimental for the response. The reason for this is that the too high field strength causes a too high current. Thus, in order to avoid the detrimental effect of a too high current, the applied voltage is decreased in a pseudo-exponential way, and the electrical current is limited by a shut-off circuit, e.g. the terminating module 106 terminating the generation of pulses, to limit the maximum current delivered to a current in the range of 6-10 A, e.g. 6 A.

Further, investigation of the effect of applied electric pulses of 600, 800, 1000, 1200 V/cm; having 100 and 500 µs pulse length, and 2, 4, 6 or 12 pulses, on the accumulation of the radiolabeled pharmaceutical $^{99m}$Tc-DTPA that mimics the Bleomycin, in rat muscular tissue after in vivo electro-permeabilization has been performed. Gamma camera measurements is applied to noninvasively quantify the accumulation of $^{99m}$Tc-DTPA in the region treated with electrical pulses as previously described.

By statistical analysis and modelling of the data performed using multivariate data processing methods such as Principal Component Analysis (PCA), and modelled with the method of Projection to Latent Structures (PLS), also called Partial Least Square Regression (PLSR) commonly used in chemo-metrics, bio-pharmacology and related areas, the inventors surprisingly found a negative correlation of the Uptake Ratios (UR) after 6 and 24 hours with the amplitude of the applied electric field according to the equations:

$$UR(6h)=1{,}709-1.32 \cdot 10^{-3} \times E(V/cm)+7.67 \cdot 10^{-3} \times PL(\mu s)+0.571 \times N(pulses)$$

$$UR(24h)=12{,}342-5.87 \cdot 10^{-3} \times E(V/cm)-2.01 \cdot 10^{3} \times PL(\mu s)+0.409 \times N(pulses)$$

Exemplifying Embodiments of a Dynamic Electric Pulse-Generating Device, e.g. the Pulse Generating Device 100

The driver unit 105a controlled by an integrated computer, e.g. the processor 110, may generate rectangular pulses by a coded signal that determines a high voltage, e.g. in the range of 300-1200 V, and a low voltage, e.g. 0 V, as well as the duration of the pulse and delivering rate of a pulse-train. Thus, of the two-electrode outputs one is at high positive potential and the other at zero potential during the pulse. The pulse generator unit, e.g. the pulse generator 105, may be equipped with several driver units 105a, one for each electrode 201,202, controlled by the integrated microcomputer, e.g. the processor 110. The pulse generating device 100 may be programmed to reach several arbitrary electrode combinations and pulse train patterns for diagnostics as well as for treatment.

Figure 4:
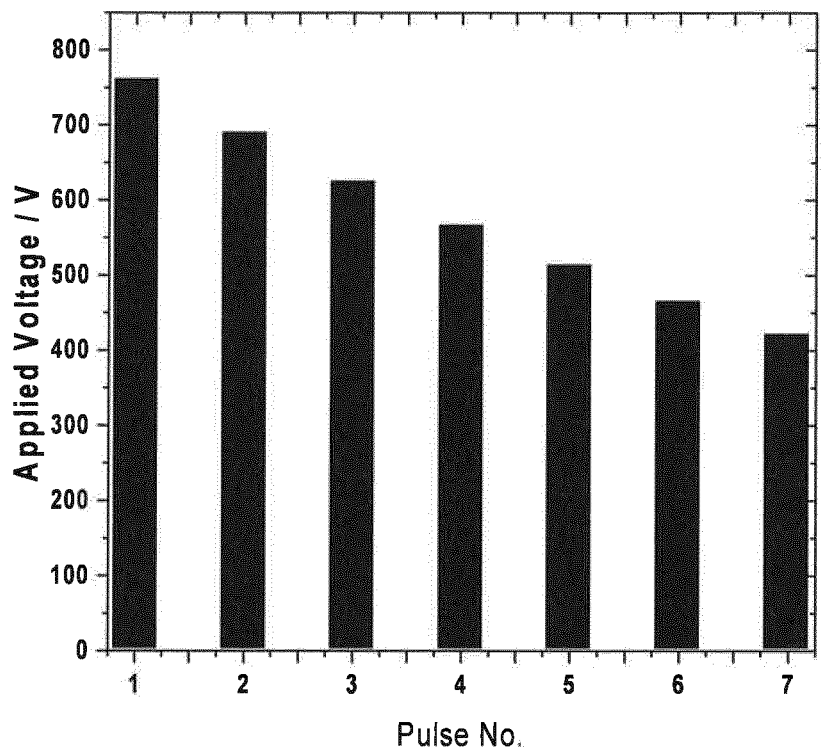
FIG. 4 schematically illustrates a pre-programmed pulse sequence with a pseudo exponentially decreasing voltage.

The dynamic electro-enhancement pulse train may originate by a capacitor (C) discharge device 105b which is loaded by a high voltage power supply. As previously mentioned, the capacitor 105b may be comprised in the pulse generator 105. If the capacitor 105b has a low capacitance the voltage of succeeding pulses decrease rapidly, e.g. with a large constant $f_C$, in an exponential way, such as approximately $\exp(-f_C \cdot time)$. Since the constant $f_C$, being equal to the characteristic frequency $f_C=\sigma/C$, is depending on the conductivity of the tissue a, alternatively a pre-programmed pulse sequence with a constant set by the pulse generating device 100 may be applied to get a pseudo exponentially decreasing voltage. This constant may be varied for various types of tumours to get the most optimal treatment. FIG. 4 schematically illustrates an example of a pre-programmed pulse sequence with a pseudo exponentially decreasing voltage.

The capacitor (C) 105b, loaded to the pre-set voltage, may be connected to the electrode device 200 inserted in the subject to be treated and discharged stepwise to create a pulse train where the voltage of the pulses gradually decrease pseudo exponentially. The current in each pulse increase gradually, but are not allowed to exceed a pre-set level of e.g. 6-10 A. If this level is reached the pulsing immediately stop. This dynamic electro pulsing create highly reversible permeability of the cell membranes and enhanced immune response.

It should be understood that different pre-programmed treatment protocols may be selected. For example, the protocol may be a European Standard Operating Procedures of Electrochemotherapy (ESOPE) protocol, a Reversible Discharging capacitance protocol using a mono-polar pulse, a Reversible Dynamic Pre-programmed protocol using pseudo-exponentially decreasing voltage bi-polar pulses, and a Reversible Dynamic Protocol for the oral-cavity using pseudo-exponentially decreasing voltage bi-polar pulses, just to give some example.

By an ESOPE protocol is meant a protocol according to which 8 mono-polar pulses of 1000 V amplitude and with 100 µs pulse length are delivered at a rate of 5 kHz to needle electrodes 10 mm apart.

By a reversible discharging capacitance protocol using a mono-polar pulse is meant a protocol according to which mono-polar pulses, each 0.1 ms long, are delivered by a reduced capacitance that result in successive reduced voltage controlled by limited current in the pulse and total specific absorbed power.

By a Reversible Dynamic Pre-programmed protocol using pseudo-exponentially decreasing voltage bi-polar pulses is meant a protocol according to which bipolar pulses, each 0.1 ms long, are delivered by a pre-programmed successive pseudo-exponential reduced voltage, controlled by limited current in the pulse and total specific absorbed power.

By a Reversible Dynamic Protocol for the oral-cavity using pseudo-exponentially decreasing voltage bi-polar pulses is meant a protocol according to which bipolar pulses, each 0.1 ms long, are delivered by a pre-programmed successive pseudo-exponential reduced voltage controlled by limited current in the pulse and total specific absorbed power.

Figure 5:
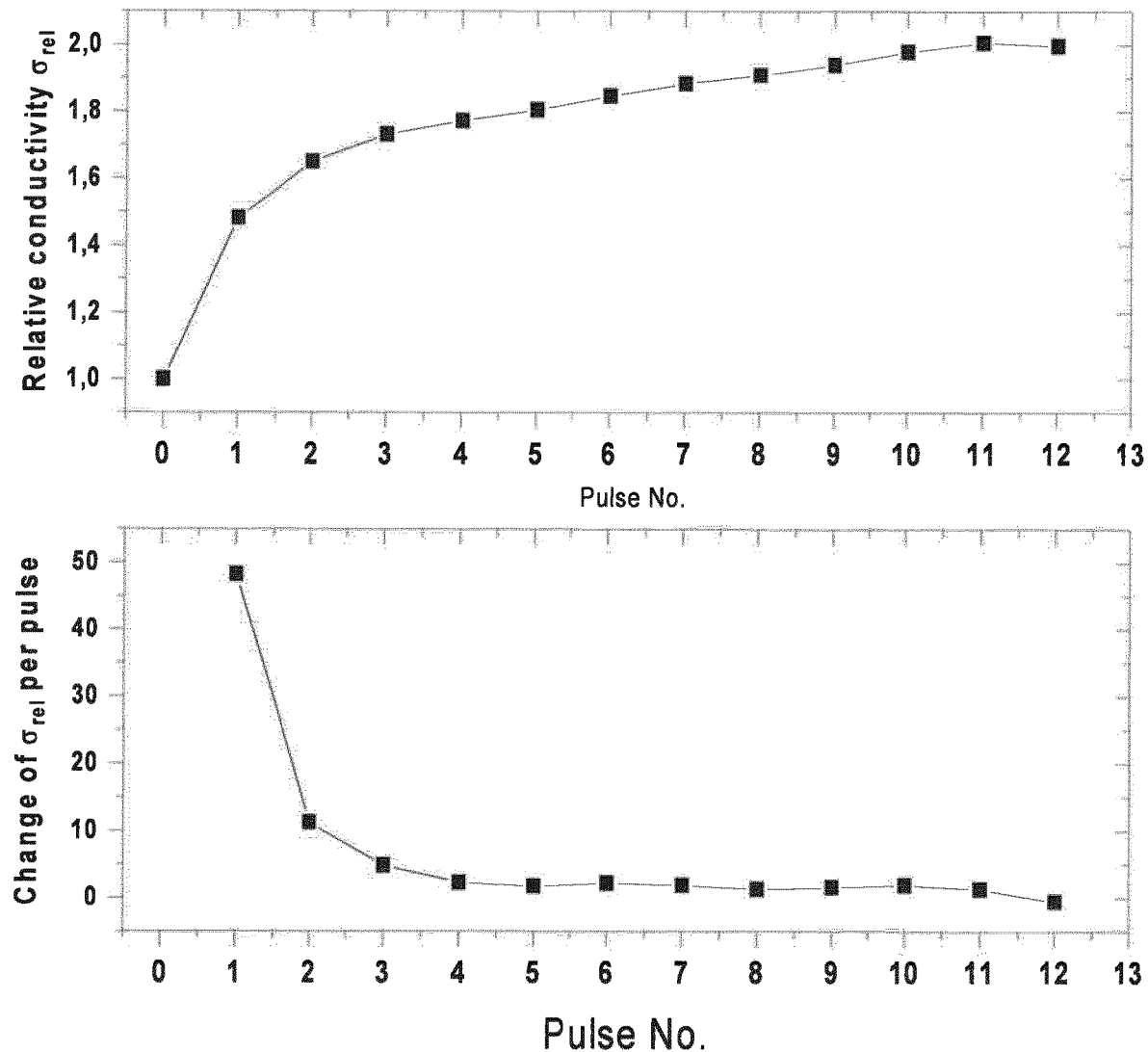
FIG. 5 schematically illustrates in the upper diagram the relative conductivity recorded during each pulse and in the lower diagram the conductivity change caused by each consecutive pulse.

In FIG. 5 the upper diagram schematically shows the relative conductance recorded during each pulse and the lower diagram shows the conductivity change caused by each consecutive pulse. The diagrams in FIG. 5 show that the main increase of tissue conductance is achieved after the first three pulses and that the following pulses give only a minor further increase, but the absorbed electric power adds detrimental inflammatory effects to the tissue that enhance the immune suppression.

As previously mentioned, the specific absorbed energy $SE_p$ delivered by each pulse is equivalent to the electro-dose per pulse:

$$SE_p = \frac{J^2 \cdot t_p}{\sigma \cdot \rho} [J \cdot kg^{-1}]$$

wherein $\sigma$ is the conductivity recorded during the pulse (S·m$^{-1}$), p is the tissue density (1060 kg·m$^{-3}$), J is the current density (A·m$^{-2}$), and $t_p$ is the length of the applied pulse (s).

Table 1 below shows how the specific absorbed energy SE delivered by each pulse with the same applied amplitude increases. As illustrated in the upper diagram of FIG. 5, the conductivity increases after each delivered pulse. The specific absorbed energy SE is sometimes herein also referred to as the electro-dose.

TABLE 1

Experimental values of absorbed energy per pulse $SE_p$, and consecutive cumulative absorbed energy, e.g. consecutive cumulative electro-dose, SE (J · kg$^{-1}$)

| Pulse No. | Average J · kg$^{-1}$ | Std. dev. | SE J · kg$^{-1}$ |
|---|---|---|---|
| 0 | 0 | 0 | 0 |
| 1 | 209 | 25 | 209 |
| 2 | 230 | 31 | 439 |
| 3 | 238 | 35 | 676 |
| 4 | 243 | 37 | 919 |
| 5 | 249 | 38 | 1168 |
| 6 | 254 | 40 | 1422 |
| 7 | 260 | 41 | 1682 |
| 8 | 265 | 41 | 1947 |
| 9 | 270 | 41 | 2216 |
| 10 | 275 | 43 | 2491 |
| 11 | 279 | 43 | 2770 |
| 12 | 278 | 42 | 3048 |

The specific energy per pulse delivered by the exceeding four pulses cause minor contribution to the electroporation, as seen from FIG. 5. Therefore, in embodiments herein, the DEECT protocol involves a second limiting criterion: that the cumulative electro-dose "SE" (J·kg$^{-1}$) should be below a certain limit, e.g. below a desired threshold value for the total absorbed energy. The desired threshold value for the total absorbed energy may be approximately in the range of 1 000-10 000 J·kg$^{-1}$, e.g. in the range of 1 000-2 000 J·kg$^{-1}$. However, an optimal threshold value may be derived based on information and values stored in a memory, e.g. the memory 109, such as a database.

Exemplifying Embodiments of the Database, e.g. the Memory 109

Patient data and other descriptors for the treatment, such as treatment configuration and type of electrodes, e.g. the needle electrodes 201,202, a distance between the electrodes in an electrode pair, the applied voltage over each electrode pair configuration as well as the recorded voltage and current values during each pulse etc., may be stored as treatment descriptor variables in the data base of the pulse generating device 100.

Further, the database may store conductivity values for various organs, tissues and tumours, which may be used to set the pre-treatment conductivity for the tissue to be treated and the limit value for the absorbed energy.

The response of the treatment at each follow up occasion, and any side effects may be recorded as dependent variables.

The database may be regularly modelled using second generation multivariate statistical methods in order to generate and update the values of the limiting factors for the pulse parameters, current and absorbed energy (J·kg$^{-1}$) in order to achieve optimal treatment descriptors and current density during the treatment.

For example, the threshold values of the current I and the specific absorbed energy SE may be determined by clinical experience and may be in the range of I=4-10 A, SE=1000-10000 J/kg, e.g. SE=1000-2000 J/kg.

When the word "comprise" or "comprising" is used in this disclosure it shall be interpreted as non-limiting, i.e. meaning "consist at least of".

Modifications and other variants of the described embodiment(s) will come to mind to one skilled in the art having the benefit of teachings presented in the foregoing descriptions and the associated drawings. Therefore, it is to be understood that the embodiment(s) herein is/are not be limited to the specific examples disclosed and that modifications and other variants are intended to be included within the scope of this disclosure. Although specific terms may be employed herein, they are used in a generic and descriptive sense only and not for purposes of limitation.

The invention claimed is:

1. A device for delivery of electrical pulses to a desired tissue of a mammal, wherein the device comprises a pulse generating device and at least two needle electrodes configured to be arranged at the desired tissue of the mammal, wherein the pulse generating device is configured to be connected to the at least two needle electrodes, and wherein the pulse generating device comprises:

a determining module configured to determine a primary voltage amplitude of a first electrical pulse to be generated between the at least two needle electrodes, and to determine a number of consecutive electrical pulses to be generated;

a pulse generator in electrical communication with the at least two needle electrodes and configured to generate one or more of the determined number of consecutive electrical pulses such that the generated first electrical pulse has the primary voltage amplitude and that the one or more generated consecutive electrical pulses have a respective voltage amplitude consecutively decreasing between consecutively generated electrical pulses; and wherein:

a feedback module configured to determine a respective absorbed energy caused in the desired tissue of each one of the one or more generated electrical pulses having the respective voltage amplitude consecutively decreasing between consecutively generated electrical pulses and configured to send information relating to the determined respective absorbed energy, and possibly the respective generated electrical pulse, to a terminating module comprised in the pulse generating device, and by:

the terminating module being configured to determine a total absorbed energy based on the received information relating to the determined respective absorbed energy, to determine whether or not the total absorbed energy exceeds a desired threshold value, and to terminate generation of the one or more of the determined number of electrical pulses when a value of the total absorbed energy, caused in the desired tissue by the one or more generated electrical pulses, exceeds the desired threshold value.

2. The pulse generating device according to claim 1, wherein the primary voltage amplitude of the first electrical pulse corresponds to a first current of the first electrical pulse that is within a desired current interval.

3. The pulse generating device according to claim 2, wherein the terminating module further is configured to terminate generation of the one or more of the determined number of electrical pulses when one of the respective current values of the generated electrical pulses is outside the desired current interval.

4. The pulse generating device according to claim 1, wherein the pulse generator is configured to generate the one or more of the determined number of consecutive electrical pulses with a respective voltage amplitude that is decreasing with a pre-set amplitude value between two consecutive electrical pulses, wherein the pre-set amplitude value is in the range of 100-1200V, e.g. 400-1200V.

5. The pulse generating device according to claim 1, wherein the pulse generator is configured to generate the one or more of the determined number of consecutive electrical pulses with a respective voltage amplitude that is exponentially decreasing between two consecutive electrical pulses.

6. The pulse generating device according to claim 5, wherein the respective voltage amplitude is exponentially decreasing between two generated consecutive electrical pulses as a function of $e^{-f_C \cdot t}$, wherein $f_C = \sigma/C$, $\sigma$, where a is the conductivity of the desired tissue, C is the capacitance of a capacitor of the pulse generator, and t is the time between the two generated consecutive electrical pulses.

7. The pulse generating device according to claim 1, wherein the determining module is configured to determine the primary voltage amplitude of the first electrical pulse to be generated between the at least two needle electrodes and the number of consecutive electrical pulses to be generated based on the conductivity a of the desired tissue, a current limit value and a Modification Factor, MF.

8. The pulse generating device according to claim 1, wherein the feedback module is configured to determine the respective absorbed energy as a respective absorbed specific energy for each pulse given by the equation:

$$SE_p = \frac{J^2 \cdot t_p}{\sigma \cdot \rho} \text{ given J/kg,}$$

wherein p identifies the applied pulse, $\sigma$ is the conductivity of the desired tissue given in S/m, J is the current density A/m², $\rho$ is the tissue density given in 1060 kg/m³, and $t_p$ is the length of the applied pulse given in seconds.

9. The pulse generating device according to claim 1, wherein the feedback module is configured to retrieve or receive a respective current of each one of the one or more generated electrical pulses and to send information relating to the determined respective current, and possibly the respective generated electrical pulse, to the terminating module.

10. A method performed by a device for delivery of electrical pulses to a desired tissue of a mammal, wherein the device comprises a pulse generating device and at least two needle electrodes configured to be arranged at the desired tissue of the mammal, wherein the pulse generating device is configured to be connected to the at least two needle electrodes, and wherein the method comprises:

determining a primary voltage amplitude of a first electrical pulse to be generated between the at least two needle electrodes, and a number of consecutive electrical pulses to be generated;

by means of a pulse generator comprised in the pulse generating device and in electrical communication with the at least two needle electrodes, generating one or more of the determined number of consecutive electrical pulses such that the generated first electrical pulse has the primary voltage amplitude and such that the one or more generated consecutive electrical pulses have a respective voltage amplitude consecutively decreasing between consecutively generated electrical pulses;

by means of a feedback module comprised in the pulse generating device, determining a respective absorbed energy caused in the desired tissue of each one of the one or more generated electrical pulses having the respective voltage amplitude consecutively decreasing between consecutively generated electrical pulses and sending information relating to the determined respective absorbed energy, and possibly the respective generated electrical pulse, to a terminating module comprised in the pulse generating device, and by means of the terminating module, determining a total absorbed energy based on the received information relating to the determined respective absorbed energy, determining whether or not the total absorbed energy exceeds a desired threshold value, and terminating the generation of the one or more of the determined number of electrical pulses when a value of the total absorbed energy, caused in the desired tissue by the one or more generated electrical pulses, exceeds a desired threshold value.

11. A computer program, comprising instructions which, when executed on at least one processor, causes the at least one processor to carry out the method according to claim 10.

12. A carrier comprising the computer program of claim 11, wherein the carrier is one of an electronic signal, an optical signal, a radio signal, or a computer readable storage medium.

* * * * *